United States Patent [19]

Drivon et al.

[11] Patent Number: 4,806,684

[45] Date of Patent: Feb. 21, 1989

[54] PROCESS FOR THE PREPARATION OF BROMOFLUOROACETIC ACIDS

[75] Inventors: Gilles Drivon, Saint-Martin-en-Haut; Bernard Gurtner, Grenoble, both of France

[73] Assignee: Atochem, Puteaux, France

[21] Appl. No.: 903,550

[22] Filed: Sep. 3, 1986

[30] Foreign Application Priority Data

Sep. 13, 1985 [FR] France ............................... 85 13611

[51] Int. Cl.⁴ .............................................. C07C 51/00
[52] U.S. Cl. ..................................... 562/605; 562/603
[58] Field of Search ........................ 562/605, 604, 603

[56] References Cited

U.S. PATENT DOCUMENTS 3,130,222  4/1964  Asadorian et al. .................. 260/539

FOREIGN PATENT DOCUMENTS 1381353  2/1964  France .

OTHER PUBLICATIONS

Streitwieser et al., Introduction to Organic Chemistry, N.Y., 1976, pp. 473–477.

Chemical Abstracts, vol. 90, No. 3, Jan. 15, 1979, No. 22332V.

*Primary Examiner*—Michael L. Shippen
*Attorney, Agent, or Firm*—Pennie & Edmonds

[57] ABSTRACT

The invention relates to the synthesis of bromofluoroacetic acids of formula:

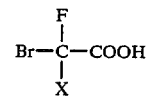

in which X is a hydrogen, fluorine, chlorine or bromine atom. These acids are prepared by reacting a compound of formula:

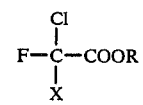

dissolved in concentrated hydrobromic acid, X having the same meaning as above and R representing a hydrogen atom or an alkyl or aryl radical, with gaseous hydrogen bromide.

19 Claims, No Drawings

PROCESS FOR THE PREPARATION OF BROMOFLUOROACETIC ACIDS

TECHNICAL FIELD

The present invention relates to the synthesis of bromofluoroacetic acids and, more particularly, to that of the acid CHFBr—COOH, which can be used as raw material for the manufacture of medicaments and plant-protection chemicals.

BACKGROUND ART

The synthesis of the acid CHFBr—COOH from trifluorochloroethylene was carried out by Haszeldine (J. Chem. Soc. 1952, 4259) in 7 successive stages and with an overall yield of only 18% according to the reaction scheme below:

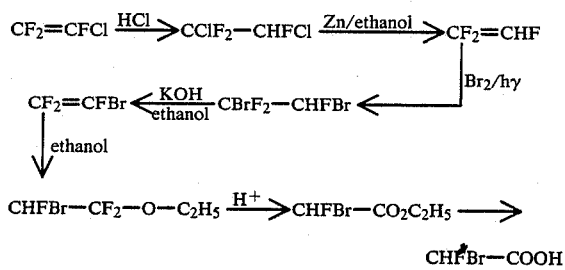

DETAILED DESCRIPTION OF THE INVENTION

It has now been found that CHFBr—COOH can be obtained from the same raw material ($CF_2$=CFCl) in a more simple way, using only three stages and obtaining an improved overal yield, by reacting an ester of chlorofluoroacetic acid (CHClF—$CO_2R$) dissolved in concentrated hydrobromic acid, with gaseous hydrogen bromide, the ester being prepared in a known way by the addition of an alcohol (ROH) to trifluorochlorethylene followed by hydrolysis of the ether CHFCl—CF$_2$—OR in an acid medium (cf. "Aliphatic Fluorine Compounds" by A. M. Lovelace et al, Reinhold Publishing Corporation, 1958, pages 157 and 234).

The third stage described above (i.e., the reaction of CHFCl—$CO_2R$ in concentrated hydrobromic medium with gaseous HBr) may be applied to chlorofluorinated compounds of formula:

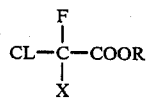

in which X represents hydrogen and R represents hydrogen, an alkyl (preferably methyl or ethyl) radical, or an aryl radical.

Therefore, the invention relates to a process for the preparation of bromofluoroacetic acids of general formula:

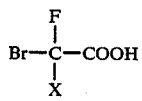

in which X has the same meaning as in formula (I) above, characterized in that a compound of formula (I) dissolved in concentrated hydrobromic acid is reacted with gaseous hydrogen bromide.

Compound (I) is first dissolved in concentrated hydrobromic acid, and then the reaction is carried out by heating the mixture while introducing gaseous hydrogen bromide, preferably with agitation (i.e., stirring). Since hydrochloric acid is insoluble in this medium, HCl gas is liberated during the reaction, along with a small amount of gaseous hydrogen bromide.

It is advantageous to use a methyl or ethyl radical as the radical R, and to heat to reflux temperature in order to remove the corresponding alkyl bromide and thus accelerate the reaction.

The concentrated hydrobromic acid used at the start may have a concentration of 45 to 60% by weight and preferably, a 48% by weight commercial grade solution is used.

The reaction is carried out preferably at atmospheric pressure, maintaining the temperature of the reaction mixture between 50° and 140° C., advantageously between 80° and 125° C.

The gaseous hydrogen bromide is preferably introduced at a rate which enables it to be completely reacted with compound (I). The progress of the reaction may be followed by measuring the amount of HCl evolved. When the reaction is complete, the bromofluoroacetic acid reaction product may be isolated by distillation of the reaction mixture under vacuum.

Although it is preferred to dissolve the compound of formula (I) directly in concentrated hydrobromic acid, the reaction may be carried out by first mixing the compound (I) with water and then injecting gaseous hydrogen bromide into this mixture to form a concentrated hydrobromic acid medium in situ, without departing from the scope of the present invention.

EXAMPLES

The following examples illustrate preferred embodiments of the invention.

EXAMPLE 1

The reaction is carried out in a 0.5-liter glass reactor equipped with a rotary stirrer, a thermometer, a gas injector and a packed column which is attached to a condenser cooled by a brine. The temperature of the condenser is maintained at between −10° and −15° C. The outlet of the condenser is equipped with a gas-liquid separator wherein the gaseous phase is connected to a water trap where evolved HCl gas is measured. 211 g of ethyl chlorofluoroacetate CFClH—$COOC_2H_5$ (1.5 mole) and 148 g of 48% by weight hydrobromic acid (0.1 liter) are introduced into this reactor. The mixture is heated to 90° C. and the injection of gaseous HBr is initiated at a rate of approximately 0.3 mole/hour. The rate of heating is adjusted to obtain a reflux at the top of the distillation column. After 7 hours of reaction (measured from the time when the temperature of the reaction mixture first reaches 90° C.), 150 g of ethyl bromide are collected at the outlet of the condenser and, at that time, the temperature of the reaction mixture is 105° C. After 13 h 30 min, the temperature has reached 120° C. with the amount of HCl gas determined in the trap corresponding to the theoretical quantity (1.5 mole). The injection of gaseous hydrogen bromide is then stopped. Under a vacuum of 50 torr absolute, hydrobromic acid (more precisely, a HBr—$H_2O$ azeotrope) distills in the first fraction and a crude CHFBr—COOH acid, which is identified and determined by NMR, is thus obtained. 168 g of the pure acid are collected by distillation of the middle fraction, under a vacuum of 22 torr absolute.

EXAMPLE 2

190 g of methyl chlorofluoacetate CHClFCOOCH₃ (1.5 mole) and 148 g of 48% by weight hydrobromic acid are introduced into an apparatus which is similar to that of Example 1, but which does not include the liquid collector at the outlet of the condenser. The mixture is heated at 80° C. to the reflux temperature and gaseous hydrogen bromide is injected at a rate of 0.3 mole/h as in Example 1. The gaseous phase at the condenser outlet contains three components: HBr, HCl and CH₃Br.

After 10 hours, the temperature of the reaction mixture is 110° C. After 15 hours, the theoretical quantity of HCl, 1.5 moles, is obtained. The injection of gaseous hydrogen bromide is then stopped and hydrobromic acid is distilled in the first fraction under vacuum.

A crude acid which is identified and determined by NMR, is obtained. 192 g of the pure acid CHFBr—COOH are collected by the distillation of the middle fraction under a vacuum of 62 torr absolute at 116° C.

EXAMPLE 3

169 g of CHFCl—COOH (1.5 mole) and 195 g of 48% strength hydrobromic acid are introduced into the same apparatus as in Example 1. The mixture is heated to 80° C. and gaseous hydrogen bromide is injected at a rate of 0.5 mole/h for 5 hours. The temperature in the reactor at the end of this procedure is 120° C. 1.2 mole of HCl are thus collected in the water trap.

Hydrobromic acid distils in the first fraction under vacuum. After analysis and distillation as in the previous example, 1 mole of CHFBr—COOH is collected.

While it is apparent that the invention wherein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

We claim:

1. A process for preparing bromofluoroacetic acid of formula:

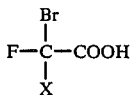

wherein X is hydrogen, which comprises reacting a compound of the formula (I):

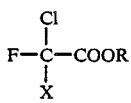

wherein R is group, with gaseous hydrogen bromide in a concentrated hydrobromic acid medium at a sufficient temperature and pressure and for a sufficient time to obtain bromofluoroacetic acid.

2. The process according to claim 1, wherein R is a methyl or ethyl group.

3. The process according to claim 1 wherein the alkyl group forms an alkyl bromide which is removed to form the acid.

4. The process according to claim 1 wherein the concentrated hydrobromic acid medium is a 45 to 60% by weight aqueous solution of hydrobromic acid.

5. The process according to claim 1 wherein the temperature of the reaction mixture is between about 50° and 140° C.

6. The process according to claim 1 wherein the reaction is carried out at atmospheric pressure.

7. The process according to claim 1 wherein the concentrated hydrobromic acid medium is prepared by mixing the compound of formula (I) with water to form a solution and injecting gaseous HBr into the solution until the desired concentrated hydrobromic acid medium is formed.

8. A process for preparing bromofluoroacetic acid of formula:

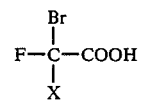

wherein X is hydrogen, which comprises reacting a compound of the formula (I):

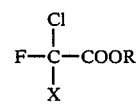

wherein R is group, with gaseous hydrogen bromide in a concentrated hydrobromic acid medium of a 45 to 60% by weight aqueous solution of hydrobromic acid at atmospheric pressure and at a temperature of between about 50° and 140° C. to obtain bromofluoroacetic acid.

9. The process according to claim 8 wherein the hydrobromic acid concentration is about 48% by weight.

10. The process according to claim 8 wherein the reaction temperature is between 80° and 125° C.

11. A process for preparing bromofluoroacetic acid of formula:

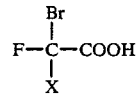

wherein X is hydrogen, which comprises:
reacting a compound of the formula (I):

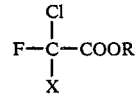

wherein R is an alkyl group, with gaseous hydrogen bromide in a concentrated hydrobromic acid medium of a 45 to 60% by weight aqueous solution of hydrobromic acid at atmospheric pressure and at a temperature of between about 50° and 140° C.;
forming an alkyl bromide; and
removing the alkyl bromide to obtain bromofluoroacetic acid.

12. A process preparing bromofluoroacetic acid of formula:

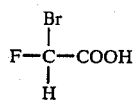

which comprises reacting a compound of the formula (I):

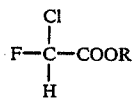

wherein R is hydrogen or an alkyl group, with gaseous hydrogen bromide in a concentrated hydrobromic acid medium at a sufficient temperature and pressure and for a sufficient time to obtain bromofluoroacetic acid.

13. The process according to claim 12 wherein the concentrated hydrobromic acid medium is a 45 to 60% by weight aqueous solution of hydrobromic acid.

14. The process according to claim 12 wherein the temperature of the reaction mixture is between about 50° and 140° C.

15. The process according to claim 12 wherein the reaction is carried out at atmospheric pressure.

16. The process according to claim 12 wherein the concentrated hydrobromic acid medium is prepared by mixing the compound of formula (I) with water to form a solution and injecting gaseous HBr into the solution until the desired concentrated hydrobromic acid medium is formed.

17. A process for preparing bromofluoroacetic acid of formula:

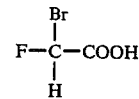

which comprises reacting a compound of the formula (I):

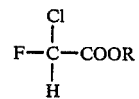

wherein R is hydrogen or an alkyl group, with gaseous hydrogen bromide in a concentrated hydrobromic acid medium of a 45 to 60% by weight aqueous soluton of hydrobromic acid at atmospheric pressure and at a temperature of between about 50° and 140° C. to obtain bromofluoroacetic acid.

18. The process according to claim 16 wherein the hydrobromic acid concentration is about 48% by weight.

19. The process according to claim 17 wherein the reaction temperature is between 80° and 125° C.

* * * * *

UNITED STATES PATENT AND TRADEMARK OFFICE
CERTIFICATE OF CORRECTION

PATENT NO. : 4,806,684
DATED : February 21, 1989
INVENTOR(S) : Gilles Drivon and Bernard Gurtner It is certified that error appears in the above-identified patent and that said Letters Patent is hereby corrected as shown below:

At column 3, line 63 and column 4, line 35 the full definition of the symbol R in the equation

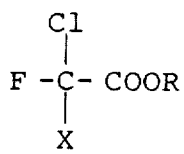

should read --R is an alkyl group-- rather than "R is group".

Signed and Sealed this

Thirteenth Day of March, 1990

Attest:

JEFFREY M. SAMUELS

*Attesting Officer*  *Acting Commissioner of Patents and Trademarks*